United States Patent [19]
Tachibana et al.

[11] Patent Number: 6,096,000
[45] Date of Patent: Aug. 1, 2000

[54] APPARATUS FOR TRANSPORT OF FLUIDS ACROSS, INTO OR FROM BIOLOGICAL TISSUES

[75] Inventors: Katsuro Tachibana; Shunro Tachibana, both of Fukuoka, Japan

[73] Assignee: Ekos Corporation, Bothell, Wash.

[21] Appl. No.: 09/103,644

[22] Filed: Jun. 23, 1998

[30] Foreign Application Priority Data

Jun. 23, 1997 [JP] Japan .................................. 9-166334

[51] Int. Cl.⁷ .................................................. A61N 1/30
[52] U.S. Cl. ............................................................ 604/20
[58] Field of Search .................................. 604/22, 20, 96, 604/131; 601/2; 606/169; 128/660.03

[56] References Cited

U.S. PATENT DOCUMENTS

| | | | |
|---|---|---|---|
| 3,635,213 | 1/1972 | La Hay .................................... | 128/2 R |
| 3,794,910 | 2/1974 | Ninke et al. ........................... | 324/30 R |
| 4,457,748 | 7/1984 | Laltin et al. ............................. | 604/20 |
| 4,702,732 | 10/1987 | Powers et al. . | |
| 4,821,740 | 4/1989 | Tachibana et al. ...................... | 128/798 |
| 4,883,457 | 11/1989 | Sibalis ...................................... | 607/20 |
| 4,953,565 | 9/1990 | Tachibana et al. ...................... | 128/798 |
| 4,982,730 | 1/1991 | Lewis, Jr. . | |
| 5,115,805 | 5/1992 | Bommannan et al. ............. | 128/24 AA |
| 5,279,543 | 1/1994 | Glikfeld et al. ........................... | 604/20 |
| 5,282,785 | 2/1994 | Shapland et al. ......................... | 604/21 |
| 5,291,887 | 3/1994 | Stanley et al. ............................ | 128/637 |
| 5,421,816 | 6/1995 | Lipkovker . | |
| 5,582,586 | 12/1996 | Tachibana et al. . | |
| 5,693,016 | 12/1997 | Gumaste et al. .......................... | 604/131 |

FOREIGN PATENT DOCUMENTS

| | | | |
|---|---|---|---|
| 3-170172 | 7/1991 | Japan ........................................ | 604/20 |
| 0654254 | 3/1979 | U.S.S.R. .................................... | 604/20 |
| 0931191 | 5/1982 | U.S.S.R. ..................................... | 601/2 |
| 1003853 | 3/1983 | U.S.S.R. .................................... | 604/20 |
| 1103863 | 7/1984 | U.S.S.R. .................................... | 604/20 |
| 1146059 | 3/1985 | U.S.S.R. .................................... | 604/20 |
| 91/12772 | 9/1991 | WIPO . | |
| WO 98/00194 | 1/1998 | WIPO ........................... | A61M 37/00 |

OTHER PUBLICATIONS

"Development of TTS Drugs in the United States", Morimoto, Therapeutic Research, vol. 10, No. 3, 1989.
"Skinside Out", Scientific American, Nov. 1991, pp. 93–94.

Primary Examiner—Wynn Wood Coggins
Assistant Examiner—Eric Kline
Attorney, Agent, or Firm—Wilson Sonsini Goodrich & Rosati

[57] ABSTRACT

An apparatus for creating holes in a biological tissue is disclosed. The apparatus includes a housing which at least partially defines a fluid chamber. The fluid chamber including a tissue contact surface which is configured to be positioned adjacent the biological tissue. An ultrasound delivery device is positioned adjacent the fluid chamber and is configured to cavitate a fluid within the fluid chamber. A plurality of apertures extend from the fluid chamber through the tissue contact surface. The apertures are sized to permit passage of the cavitated fluid through the apertures.

44 Claims, 9 Drawing Sheets

APPARATUS FOR TRANSPORT OF FLUIDS ACROSS, INTO OR FROM BIOLOGICAL TISSUES

RELATED APPLICATIONS

This application claims priority to Japanese application number 9-166334, entitled Apparatus and filed Jun. 23, 1997 which is incorporated herein by reference in its entirety.

BACKGROUND OF THE INVENTION

1. Field of the Invention

The present invention relates to a an apparatus for transporting fluids across, into or from tissues and more particularly for transporting biological fluids across, into or from biological tissues.

2. Description of Related Art

The ability to transport fluids across, into or from biological tissues plays an important role in many medical procedures. For instance, many medical treatments require that blood be withdrawn across a patient's skin or that medicament be administered to a patient by injecting the medicament across the patient's skin. There are known methods of administering medicament transdermally via diffusion through the skin. However, the skin has protective functions that prevent the intrusion of foreign matter from outside, so merely coating the skin with medicament is not sufficient for the medicament to be absorbed efficiently.

Biological fluids can be collected and medicaments can be administered using a hypodermic needle. However, hypodermic needles are associated with a risk of infection and are known to be painful. It is also known to collect fluids through the skin of a patient by applying a vacuum suction apparatus to the skin, however, vacuum suction apparatuses are known to have poor efficiency and to leave suction marks remaining on the skin.

Many of the problems described above also result when fluids are transported across, into or from other biological tissues such as the walls of blood vessels or the surface of organs.

There is a need for a method and apparatus capable of efficiently transporting fluids across, into or from a tissue without causing pain or leaving marks upon the patient.

SUMMARY OF THE INVENTION

An apparatus for creating holes in a biological tissue is disclosed. The apparatus includes a housing which at least partially defines a fluid chamber. The fluid chamber including a tissue contact surface which is configured to be positioned adjacent the biological tissue. An ultrasound delivery device is positioned adjacent the fluid chamber and is configured to cavitate a fluid within the fluid chamber. A plurality of apertures extend from the fluid chamber through the tissue contact surface. The apertures are sized to permit passage of the cavitated fluid through the apertures.

In another embodiment, the apparatus includes a housing which at least partially defines a fluid chamber. The fluid chamber includes a tissue contact surface which is configured to be positioned adjacent the biological tissue. An ultrasound delivery device is positioned adjacent the fluid chamber and is configured to operate at a frequency which cavitates a fluid within the fluid chamber. A plurality of apertures extend from the fluid chamber through the tissue contact surface. The apertures have a size matched to have the fluid exit from the chamber through the apertures at the operating frequency of the ultrasound delivery device.

In another embodiment, the apparatus includes an elongated body which includes a distal end which at least partially defines a fluid chamber. A tissue contact surface is included in the elongated body and is configured to be positioned adjacent the biological tissue. An ultrasound delivery device is positioned within the fluid chamber and is configured to cavitate a fluid within the fluid chamber. A plurality of apertures extend from the fluid chamber through the tissue contact surface. The apertures are sized to permit passage of the cavitated fluid through the apertures.

DETAILED DESCRIPTION

Figure 1:
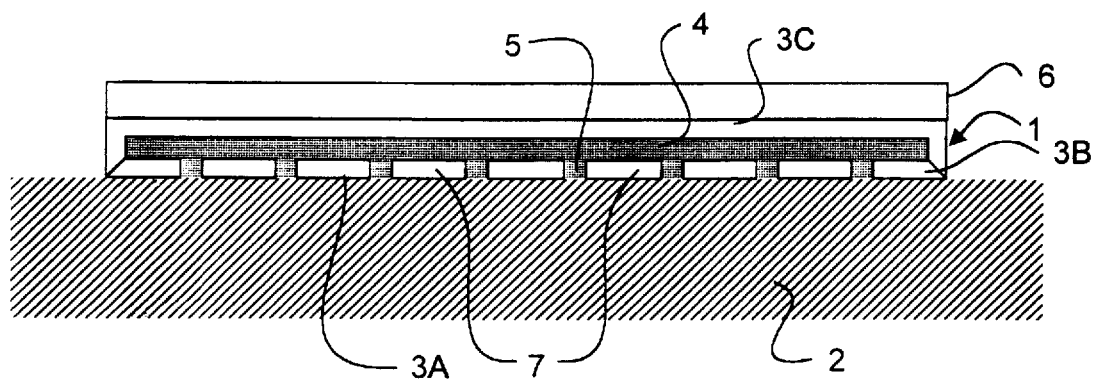
FIG. 1 is a is a cross section of an apparatus for transporting a fluid across, into or from a tissue.

FIG. 1 illustrates an apparatus 1 for transporting fluids across, into or from a tissue 2. A tissue contact surface 3A is included in a distal member 3B which is part of a housing 3C. The housing 3C defines a fluid chamber 4. The housing 3C and/or the distal member 3B can be constructed from hard materials including, but not limited to, plastics, hard resin, aluminum, iron, stainless steel, etc. The housing 3C and/or the distal member 3B can also be constructed from softer more flexible materials including, but not limited to, polyvinyl chloride, polyethylene, rubber, Styrofoam, etc. The distal member 3B can be integral with the housing 3C or can be removable from the housing 3C. The distal member 3B can be constructed from the same material as the housing 3C or different materials. For instance, the distal member 3B can be constructed from a more flexible material while the housing 3C is constructed from more rigid materials. This construction allows the apparatus 1 to be pushed against a tissue 2 with sufficient force that the housing 3C retains its shape but the distal member 3B conforms to the contours of the tissue 2. The distal member 3B has a height which is preferably from 1 µm to 1 cm, more preferably from 3 µm to 1 mm.

Figure 2:
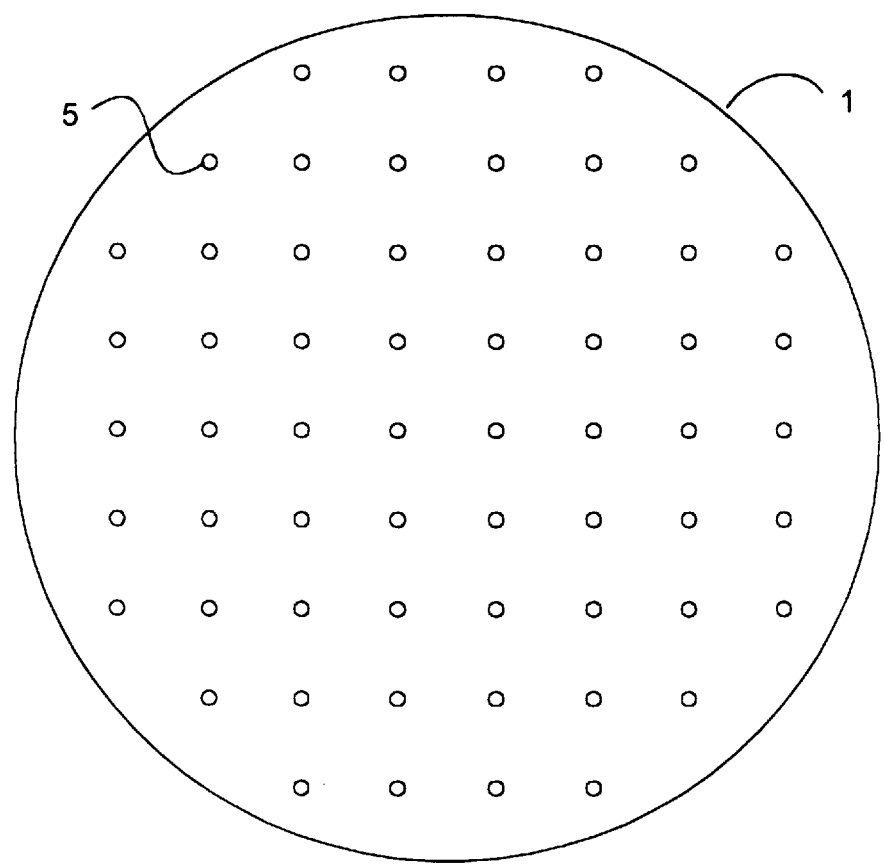
FIG. 2 is a bottom view of the apparatus illustrated in FIG. 1.

As illustrated in FIGS. 1 and 2, a plurality of apertures 5 extend from the fluid chamber 4 through distal member 3B. The apertures 5 can be uniformly distributed as illustrated in FIGS. 1 and 2 or they can be provided with nonuniform density. Suitable diameters for the apertures 5 include, but are not limited to, 0.1 µm to 3 mm and 0.3 µm 0.1 mm. In addition, the shape of the apertures 5 is not limited to circular, as they may also be star-shaped, polygonal-shaped or irregularly shaped. The density of apertures 5 can be set in the range from 1 to 1 million per square centimeter. apparatus 1 is illustrated in FIG. 2 as having a round shape, however, the apparatus 1 can have a variety of geometries including, but not limited to, square and rectangular. When the apparatus 1 has a round shape, the apparatus 1 preferably has a diameter from 1–5 cm and more preferably fro 2–4 cm.

An energy delivery device 6 is positioned adjacent the fluid chamber 4 on the opposite side of the apertures 5. The energy delivery device 6 can be integral with the housing 3C or can be detachable from the housing 3C. Suitable energy delivery devices 6 include, but are not limited to, ultrasound elements powered by lasers, electromagnetic coils, or piezoelectric polymers or ceramics. An ultrasound element may consist of electrodes attached to both sides of a piezoelectric element. The piezoelectric element can be planar, cylindrical, spherical, polygonal or any other shape appropriate for the application. Ultrasound energy can be radiated in directions perpendicular to the surface of the ultrasound element by applying a pulsed or oscillating voltage between the electrodes. The ultrasound element may be made of a film-like polymer, ceramic or other hard material. The ultrasound element is supplied with a pulse or high-frequency driving signal from a power supply (not illustrated). The ultrasound frequencies that can be used include ultrasound in the range from 10 kHz–100 MHz, 500 kH–50 MHz and 1 MHz–50 MHz. In addition, the intensity of the ultrasound energy may be in the range 0.1–1000 W/cm$^2$. The ultrasound element may be divided into two or more parts, and the ultrasound generation need not necessarily be perpendicular to the surface.

At least one temperature sensor 7 can be positioned in the distal member 3B as illustrated in FIG. 1. Each temperature sensor 7 can provide a signal indicating the temperature at the temperature sensor 7. The temperature sensors 7 can be coupled with a temperature feedback control system. The feedback control system maintains the temperature at the distal member 3B within a desired range by adjusting the level of ultrasound energy delivered from the ultrasound element in response to the signal from the temperature sensors 7. Although the temperature sensors are illustrated as positioned adjacent the tissue contact surface, they can also be positioned within the fluid containment volume, the energy delivery device or elsewhere on the apparatus 1.

Figure 3:
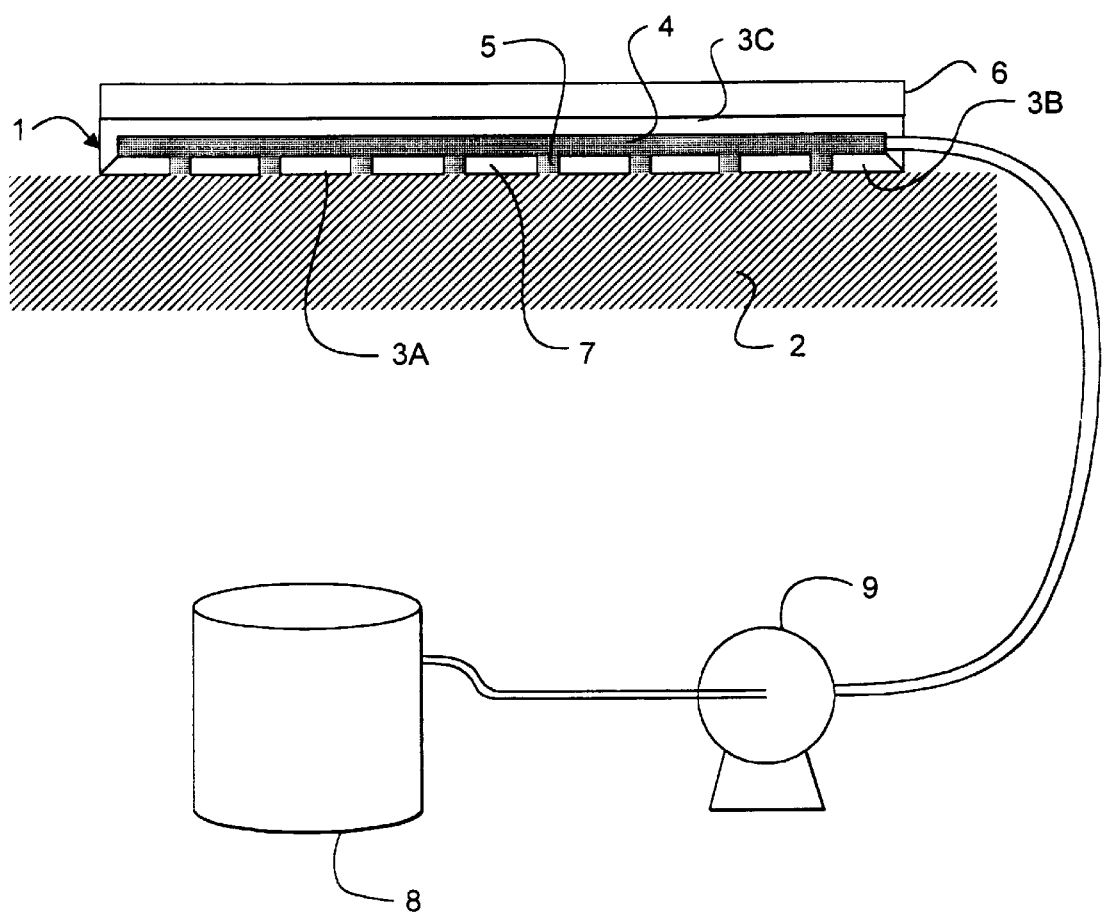
FIG. 3 illustrates an apparatus according to the present invention coupled with a fluid reservoir and a pump.

As illustrated in FIG. 3, the apparatus 1 can be incorporated into a system for transporting a fluid across, into or from a tissue 2. The system includes a fluid reservoir 8 and a pump 9. Suitable pumps 9 include, but are not limited to, a roller pump. Suitable fluid reservoirs 8 includes, but are not limited to, intravenous fluid bags typically used in hospitals and other sterile and variable volume fluid reservoirs 8. The fluid reservoir 8 is in fluid communication with the fluid chamber 4 via the pump 9. In operation, the pump 9 can be used to provide fluid to the fluid chamber 4 or can be run in reverse to draw a vacuum on the fluid chamber 4. The pump 9 is optional and can be eliminated from the system by raising and lowering the elevation of the fluid reservoir 8 relative to the apparatus 1 or by directly pressurizing the reservoir. For instance, pressurization can occur by injecting air into the reservoir with a syringe through a one-way-valve.

In operation, the fluid chamber 4 and the apertures 5 are filled with a fluid. The tissue contact surface 3A is then positioned adjacent the tissue 2. These two steps can also be performed in reverse order. For instance, the fluid chamber 4 can be filled with fluid after the tissue contact surface 3A is positioned adjacent the tissue 2. The fluid can be pumped from a fluid reservoir 8 to the fluid chamber 4.

When the apparatus 1 is positioned adjacent the tissue 2, the apparatus 1 can be pressed against the tissue 2 such that the distal member 3B at least partially conforms to the contours of the tissue 2. The conformation of the apparatus 1 to the contours of the tissue 2 can create at least a partial seal between the tissue 2 and the apparatus 1 to prevent the fluid within fluid chamber 4 from leaking out from under the apparatus 1. A seal can also be formed by applying a sealant such as a petroleum jelly to the periphery of the housing 3C before the apparatus 1 is positioned adjacent the tissue 2.

After the fluid containment region is filled with fluid and the apparatus 1 positioned adjacent the tissue 2, a pulsed driving signal is supplied to the energy delivery device 6. In response, the energy delivery device 6 deforms in the direction perpendicular to the surface of the energy delivery device 6, and a pulsed pressure is applied to the apparatus 1, causing an acoustic pressure wave to propagate through the fluid in the fluid chamber 4. The pressure waves cause changes to pressure which generate cavitation in the fluid within the fluid chamber and within the apertures.

The mechanism of cavitation is described in Robert E. Apfel: "Sonic effervescence: tutorial on acoustic cavitation," Journal of Acoustic Society of America 101 (3): 1227–1237, March 1997, Atchley A. Crum L: "Ultrasound-Its chemical, physical and biological effects: Acoustic cavitation and bubble dynamics," Ed. Suslick K, pp. 1–64, 1988 VCH Publishers, New York. These references are incorporated herein by reference in their entirety and are described briefly below.

FIGS. 4A–4D illustrate the generation of cavitation within the fluid chamber 4 and aperture 5. Cavitation is a phenomenon in which bubbles formed from gas dissolved in a fluid under acoustic vibrations or bubbles that are already present oscillate or repeatedly expand and contract. This cavitation does not occur uniformly within the fluid but it occurs most often in locations where the fluid is in close proximity to a solid interface. As a result, the bubbles are most often formed within the apertures in the distal member 3B.

Figure 4A:
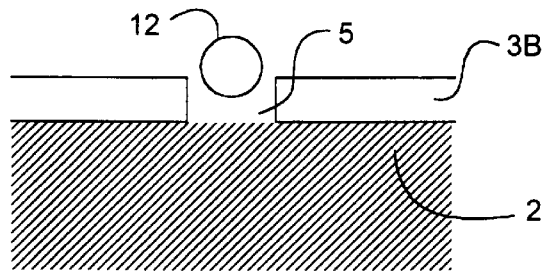
FIGS. 4A–4D illustrates the process of cavitation within the fluid chamber.
Figure 4B:
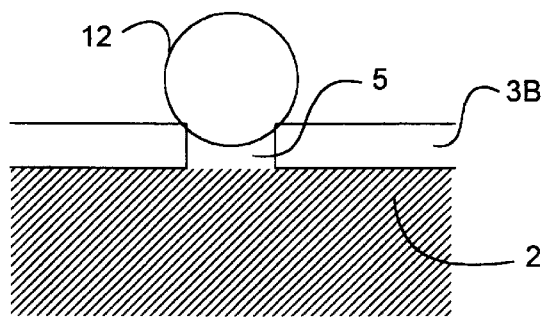
Figure 4C:
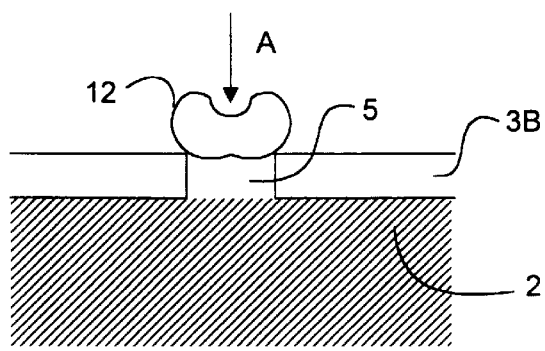
Figure 4D:
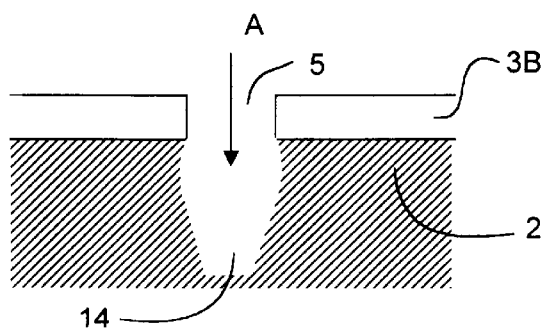

When the ultrasound energy delivered to the fluid causes the pressure of the fluid to drop rapidly, gas dissolved in the fluid forms a nearly spherical bubble 12 at an aperture 5 in the apparatus 1 as illustrated in FIG. 4A. As the pressure drops the bubble 12 grows as illustrated in FIG. 4B. If the bubble 12 grows to a size at which the spherical shape cannot be maintained, the bubble 12 collapses as illustrated in FIG. 4C. This collapse occurs on the side of the bubble 12 opposite the tissue contact surface 3A. The fluid at the top of the bubble 12 is sucked in the direction of arrow A toward the aperture 5. The bubble 12 collapses rapidly accelerating the flow of fluid at the top of bubble 12. Eventually the flow of fluid becomes a jet in the direction of arrow A. The jet strikes the surface of the tissue 2 at roughly 600 km/h. This causes a fine hole 14 to be formed in the surface of the tissue 2. Since a plurality of apertures 5 are formed in the distal member 3B, the number of holes 14 in the tissue 2 corresponds to the number of apertures 5. A suitable tissue 2 includes but is not limited to human skin. Since skin is able to heal and close tiny holes 14 of this nature in a short period of time, the apparatus 1 reduces the discomfort to the patient.

After a large number of fine holes 14 are formed in a tissue 2 such as skin by the method described above, medicament can be efficiently absorbed into the body by coating the medicament upon the treated area of the tissue 2. The amount of medicament absorbed can be controlled by changing the surface area or shape of the distal member 3B by increasing the aperture size. Similarly, the density of the apertures 5 can be increased to increase the absorption of medicament.

In addition to applying medicament to a tissue 2 after the apparatus 1 is removed, the medicament can be applied via the apparatus 1 by including the medicament within the fluid chamber 4 or the fluid reservoir 8. The cavitation serves to transport the medicament past the tissue 2 by injecting the medicament containing fluid through the holes 14. Different frequencies can be used for creation of the holes and delivery of the medicament containing fluid through the holes. For instance, the frequency which is optimal for hole creation may be different than the frequency which is optimal for the delivery of a particular medicament.

Suitable medicaments which can be included within the fluid or can be applied to the tissue 2 include, but are not limited to, insulin, anti-cancer drugs, vitamins, minerals, saline solution, various hormones (growth hormone, female sex hormones, antidiuretic hormone), steroids, anti-inflammatory drugs, anti-allergic drugs, photosensitizing agents, contrast media, various proteins, genes, viruses, lidocaine or other local anesthetics, drugs used for general anesthesia, general painkillers, various psychotropic drugs, tranquilizers, anticoagulant factors (heparin, urokinase), albumin, antibiotics, antihypertensive agents, vasopressor drugs, anti-psoriasis drugs, or in the case of internal tissues and vessels anti-proliferative agents, anti-restenosis agents, anti-neoplastic agents, anti-oncological agents, etc.

After the holes 14 are formed in the tissue 2, biological fluids can also be drawn from the tissue 2 into the fluid chamber 4. To draw biological fluids across or from the tissue 2 a vacuum is applied to the fluids within the fluid chamber 4. The pump 9 illustrated in FIG. 3 can be used to create this vacuum. A portion of the biological fluids which are withdrawn will be intermixed with the fluid which was initially within the fluid chamber 4. However, the biological fluid can be withdrawn until the withdrawn fluid is partially or substantially all biological fluid. When the desired portion of biological fluids is obtained, the withdrawn fluid can be sampled for testing or other purposes. The fluid which is initially within the fluid chamber is chosen to be compatible with the fluid being sampled. For instance, the fluid initially within the fluid chamber can be physiological saline. Because the holes 14 created by the apparatus 1 are very fine, the administration of medicament or collection of bodily fluids can be performed effectively without excessive pain to the patient.

The aperture density can be customized for particular tissues. For example, to administer medicament selectively to specific areas of the skin, one can intentionally place an area with a high density of apertures 5 upon the target area. Conversely, if there are areas of the skin where medicament is not to be administered, then areas with no apertures 5 can be placed on that area. The size of the apertures 5 can be set to determine the rate of administration of medicament. In this manner, the rate, amount and area of administration of medicament can be controlled by the properties of the apertures 5. In addition, the physical properties of the medicament, for example the surface tension, viscosity, molecular weight and activity can change the conditions of administration of medicament. Moreover, the conditions of administration of medicament can also be adjusted with the number, density and shape of the apertures 5. In addition, the optimal configuration of apertures 5 is determined depending on the amount of energy, frequency, voltage, current and intensity of the ultrasound radiation.

In the exemplary embodiments described above, a pulsed driving signal is supplied to the energy delivery device 6, but a continuous driving signal may also be supplied instead. In this case, the cavitation phenomenon of bubbles 12 being generated and collapsed occurs repetitively, and a large number of holes 14 can be formed in the surface of the skin 6 with even higher efficiency.

An inverse relationship exists between the size of the apertures 5 and the optimal frequency of the ultrasound. For example, if the distal member 3B includes apertures 5 with diameters of 80 $\mu$m and 4 $\mu$m, resonance and cavitation occur most strongly around the 80-$\mu$m apertures 5 when the distal member 3B is irradiated with 40-kHz ultrasound. On the other hand, when irradiated with 1-MHz ultrasound, cavitation occurs primarily in the 4-$\mu$m diameter apertures 5. This relationship can be used to match the size of the apertures to the frequency of the ultrasound energy and vice versa. For instance, the lower frequency can be used when a large amount of medicament must be delivered. This lower frequency concentrates the cavitation at the larger apertures so an increased quantity of medicament can be delivered. Conversely, the lower frequency can be used when smaller amounts of medicament must be delivered. The medicament delivery characteristics can also be chosen by the patient or physician. For instance, the energy delivery device can be operated at a single frequency and a distal member having apertures of a uniform diameter can be selected which increases or decreases the medicament delivery rate at that frequency.

The cavitation parameters can be altered during operation of the device. For instance, if the distal member 3B is continuously irradiated with ultrasound of 1 MHz for 10 ms, bubbles 12 will be generated in the apertures 5 portions of the distal member 3B, but if the frequency of the ultrasound is immediately switched to 500 kHz, which is not the resonant frequency of the bubbles. The bubbles 12 will rupture. In this manner, by mixing a frequency-modulated wave into a single frequency, the size of the bubbles 12 when they burst can be adjusted. Similarly, the characteristics of the bubbles within the cavitated fluid can be altered by smoothly sweeping the ultrasound frequency over a range. These frequency adjustments can be used to optimize the creation of holes in the tissue or to optimize delivery of medicament into or across the tissue. For instance, the frequency can be altered to create a pumping action of the fluid into the hole The source of ultrasound energy can be controlled by computer either automatically or semi-automatically to control the dose of medicament or suction of bodily fluids. The computer can also be used to make the above frequency adjustments.

Figure 5A:
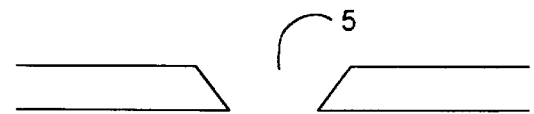
FIGS. 5A–5E illustrates cross-sections of apertures with varying shapes.
Figure 5B:
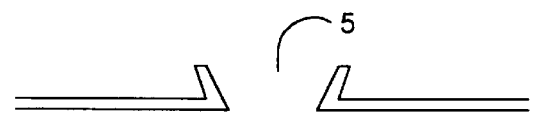
Figure 5C:
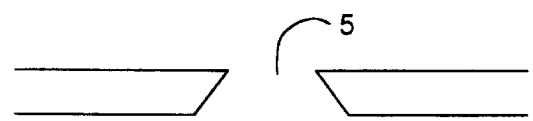
Figure 5D:
Figure 5E:
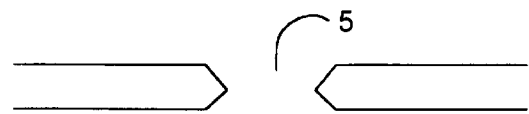

The cross-sectional shape of the plurality of the apertures in the distal member 3B of the apparatus 1 may be tapered as illustrated in FIGS. 5A–5C, or the middle of the apertures 5 may be enlarged or reduced in diameter as illustrated in FIGS. 5D–5E.

Figure 6:
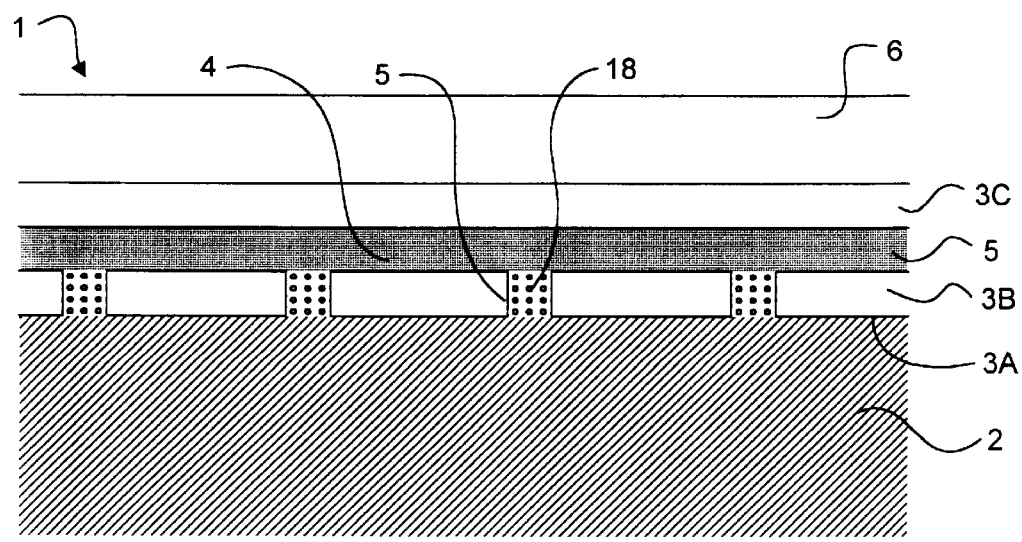
FIG. 6 is a cross section of an apparatus including a cavitation threshold reducing agent within the apertures.

The apertures 5 can be filled with cavitation threshold reducing substances 18 as illustrated in FIG. 6. Examples of cavitation threshold reducing substances 18 include rose bengal, PHOTOFRIN, Eosin Y, Erythrosine B and various surfactants, etc. Filling the apertures 5 with a cavitation threshold reducing substance 18 decreases the cavitation threshold allowing cavitation to occur at a lower ultrasound energy. The position of the cavitation threshhold producing substance within the apertures encourages cavitation within the apertures 5 where it is most desirable. As a result, the level of ultrasound energy to which the skin is exposed can be reduced. This reduced level of ultrasound energy reduces the risk of deleterious effects to the tissue 2.

The threshold value for cavitation can also be reduced by dissolving air, helium, argon, neon, perfluorocarbon or other gas within the fluid in the fluid chamber 4. This dissolved gas reduces the cavitation threshold because the air or gas becomes the seed at the time of generation of cavitation allowing the cavitation to occur easier.

Figure 7:
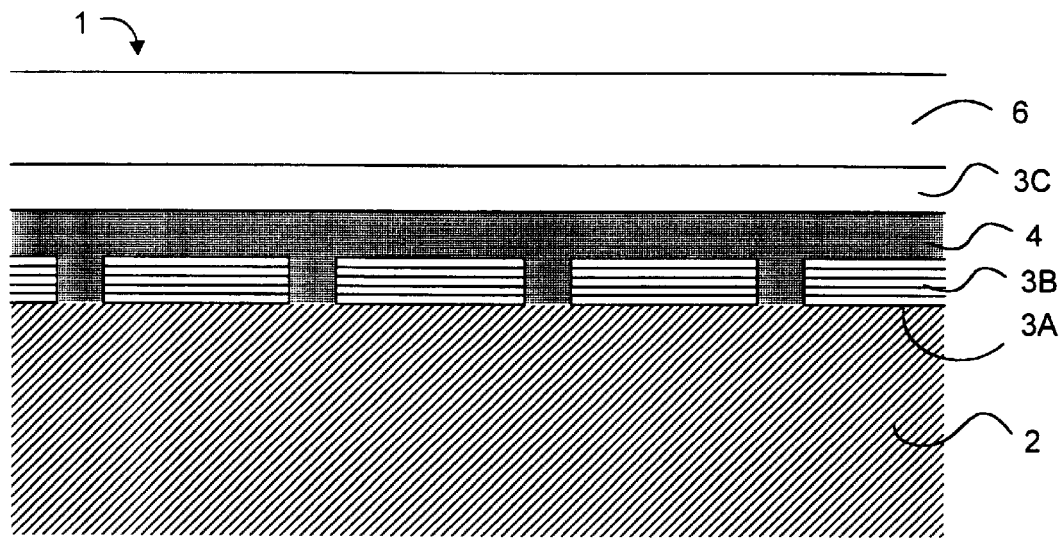
FIG. 7 is cross-section of an apparatus with a tissue contact surface constructed from ultrasound-absorbent material or ultrasound-reflective materials.

The distal member 3B of the apparatus 1 can be formed of ultrasound-absorbent material or ultrasound-reflective material as illustrated in FIG. 7. Suitable ultrasound-absorbent materials include, but are not limited to, rubber, foam rubber, etc. Suitable ultrasound-reflective materials include, but are not limited to, foam resin and other materials containing large amounts of air. The foam resin can include capsule-shaped spaces roughly 0.1 micron to 50 micron in size near the tissue contact surface 3A or throughout the entire distal member 3B. In addition, a thin layer of air 0.1 micron to 100 micron thick can be provided inside the distal member 3B. Forming the distal member 3B of ultrasound-absorbent material or ultrasound-reflective material reduces the level of ultrasound energy that the tissue 2 is exposed to by increasing the portion of ultrasound energy which is absorbed or reflected by the distal member 3B.

In conventional apparatus that is using ultrasound energy, deleterious effects on the skin such as increased temperature, heat of vibration and friction, and chemical reactions have been found. As described above, the apparatus of the present invention requires that less energy be applied to the tissue. As a result, burns and the like can be prevented. This reduced energy is derived from an increased efficiency.

Figure 8:
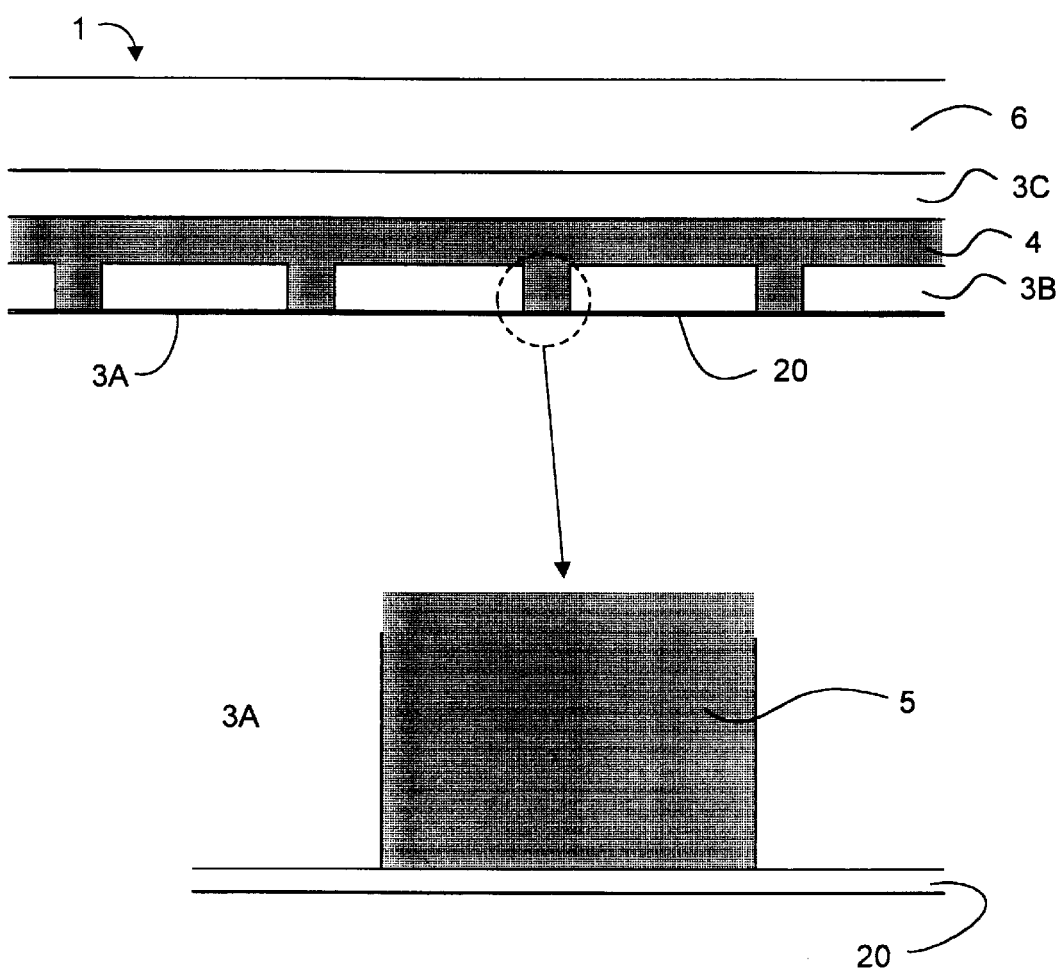
FIG. 8 is a cross-section of an encapsulation sheet which is adhered to the outside surface of the tissue contact surface.

An encapsulation sheet 20 can be adhered to the tissue contact surface 3A as illustrated in FIG. 8. The encapsulation sheet 20 can be a thin tissue adhered to the outside surface of the tissue contact surface 3A. The encapsulation sheet 20 can prevent fluid within the fluid chamber 4 from flowing out of the fluid chamber 4. The encapsulation sheet 20 can be removed before the apparatus 1 is positioned adjacent the tissue 2 or can be left in place during operation of the apparatus 1. If the apparatus 1 is operated with the encapsulation sheet 20 still attached, cavitation occurs as described above and the encapsulation sheet 20 is punctured by the jet flow generated by cavitation. As a result, the encapsulation sheet 20 does not interfere with operation of the apparatus 1.

Figure 9:
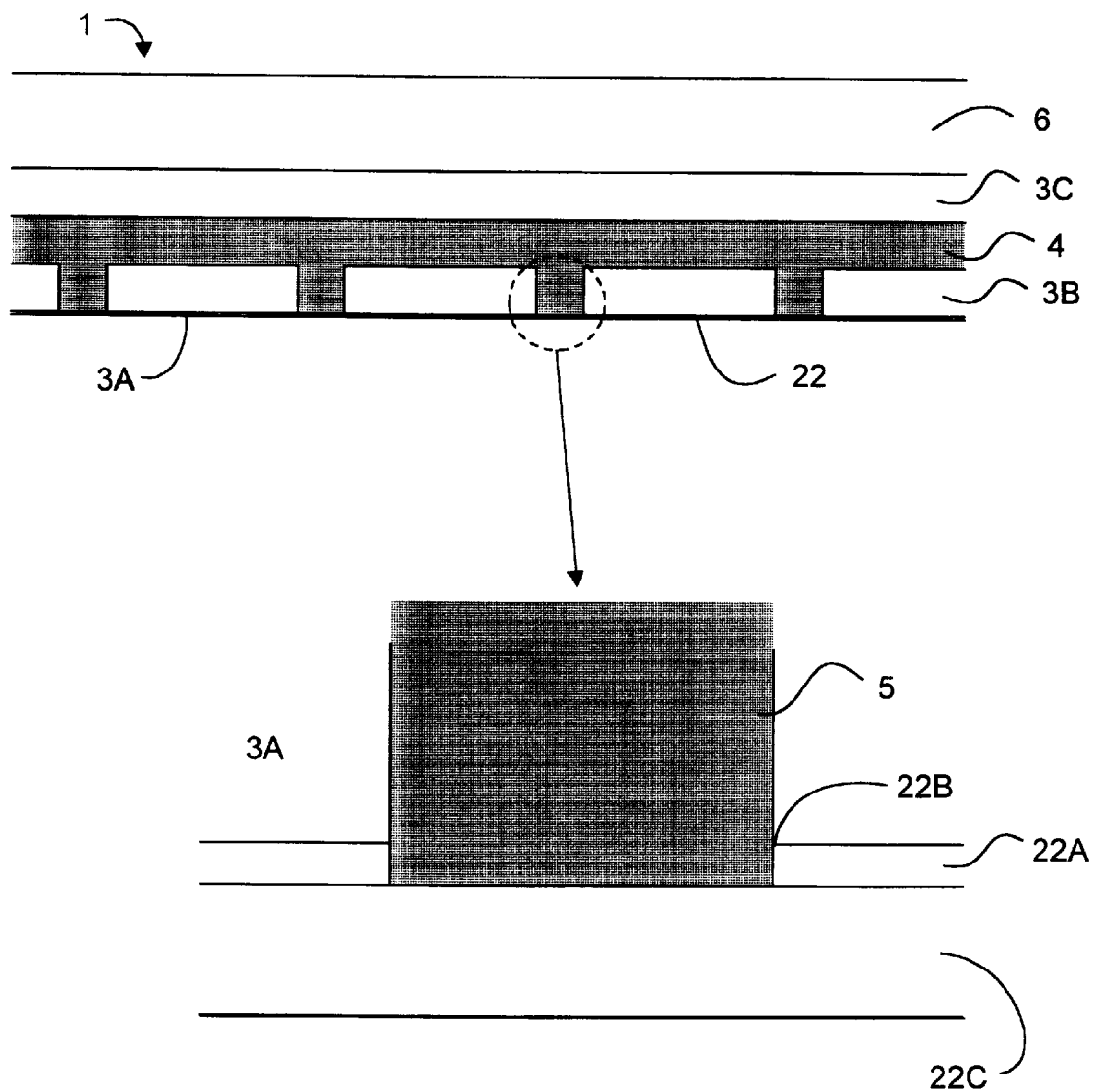
FIG. 9 is a cross-section of an apparatus including an adhesive tissue contact surface 11 attached to the outside surface of the tissue contact surface.

An adhesive patch 22 can be attached to the tissue contact surface 3A as illustrated in FIG. 9. The adhesive patch 22 consists of a layer of adhesive 22A which has holes 22B of roughly the same size as the diameter of the apertures 5 along with a peel-off backing 22C provided by lamination upon the layer of adhesive 22A.

The adhesive patch 22 is adhered to the tissue contact surface 3A to prevent leakage of fluid from the fluid chamber. Before use of the apparatus 1, the peel-off backing 22C is peeled off to expose the layer of adhesive 22B. The apparatus 1 is then secured to the tissue 2 by the adhesive force of this layer of adhesive 22B. Thereby, the apparatus 1 is secured stably to the skin so handling is simplified. In another embodiment, the adhesive is attached to the periphery of the tissue contact surface so it does not interfere with the apertures 5.

Figure 10:
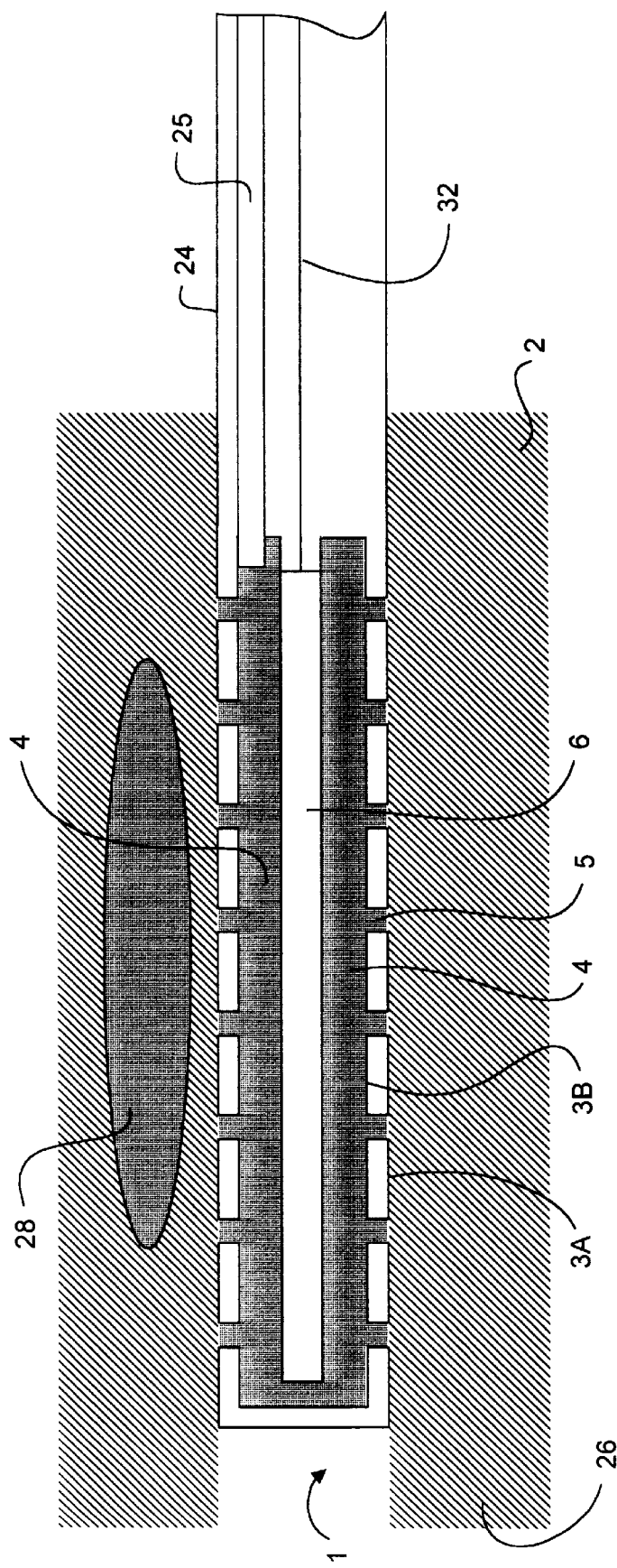
FIG. 10 illustrates an embodiment of the apparatus included on an elongated body and positioned within an esophagus.

The apparatus 1 can also be included on an elongated body 24 as illustrated in FIG. 10. A fluid delivery lumen 25 extends through the elongated body 24 and terminates within the fluid chamber. The distal member 3B has a cylinder shape which at least partially defines a flood volume 4 and a diameter matching the diameter of a body lumen 26 which includes a treatment site 28. An energy delivery device 6 is disposed within the fluid volume 4. The ultrasound element is powered by lead wires 32 extending through the elongated body 24. Suitable body lumens 26 include, but not limited to, the esophagus, cardiovascular system, bladder and urethra. A treatment site 28 can be a site within the body lumen 26 which requires that a medicament be delivered to the treatment site 28 or that biological fluids be removed from the treatment site 28. For instance, the treatment site 28 can be a tumor located adjacent a blood vessel or a diseased blood vessel itself.

In operation, the elongated body 24 is threaded through a body lumen 26 until the apertures 5 on the apparatus 1 are positioned adjacent a treatment site 28 as illustrated in FIG. 10. For instance, when the body lumen 26 is a esophagus and the treatment site 28 is a cancerous tumor, the elongated body 24 is orally inserted until the apparatus 1 is positioned adjacent the tumor. A fluid containing a cancer treatment agent is delivered to the fluid chamber 4 via the fluid delivery lumen 25. A driving signal is supplied to the ultrasound element to cause cavitation of the fluid within the fluid chamber 4 and preferably within the apertures 5. The cavitation injects the anti-cancer drug-containing fluid into the external coat of the esophagus so that a large number of holes 14 are formed in the external coat of the esophagus. Thus, the anticancer drug-containing fluid 4 absorbed via this large number of holes 14 permeates to the treatment site which may be a malignant tumor, for example. Thereby, the anti-cancer drug can be administered efficiently to the affected area. At this time, by combining an ultrasonic echo probe used for diagnosis with the apparatus 1 of the present invention, treatment can be performed while monitoring and confirming the location of the malignant tumor.

By supplying energy and anti-cancer drugs, the medicament can be allowed to permeate deeply into the tissue of the cancer of the esophagus. In addition, it is possible to cause the medicament to permeate cancer cells and the cells of other normal tissue through the cell tissues. Since the anti-cancer drugs can be administered locally, anti-cancer drugs of higher concentrations and stronger toxicity can be used. Possible anti-cancer drugs include mitomycin, Adriamycin, bleomycin and other common anti-cancer drugs, and also, the administration of medicaments (genes) used in recently developed gene therapies can be performed. Moreover, photosensitizing agents used in photochemotherapy can also be allowed to permeate into tissue. In addition, various types of contrast media can also be administered. The present invention can also be used in the treatment of colon cancer, cancers of the head and neck, brain tumors, liver cancer and lung cancer in addition to cancer of the esophagus. This apparatus 1 can also be inserted into the interior or center of the tumor for treatment.

Figure 11A:
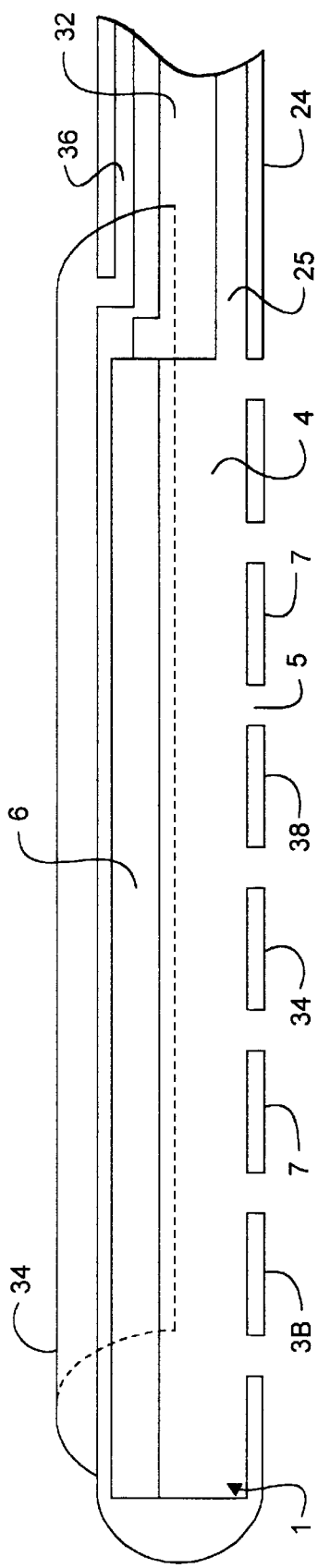
FIG. 11A is a cross section of an embodiment of the apparatus included on an elongated body which includes a balloon.
Figure 11B:
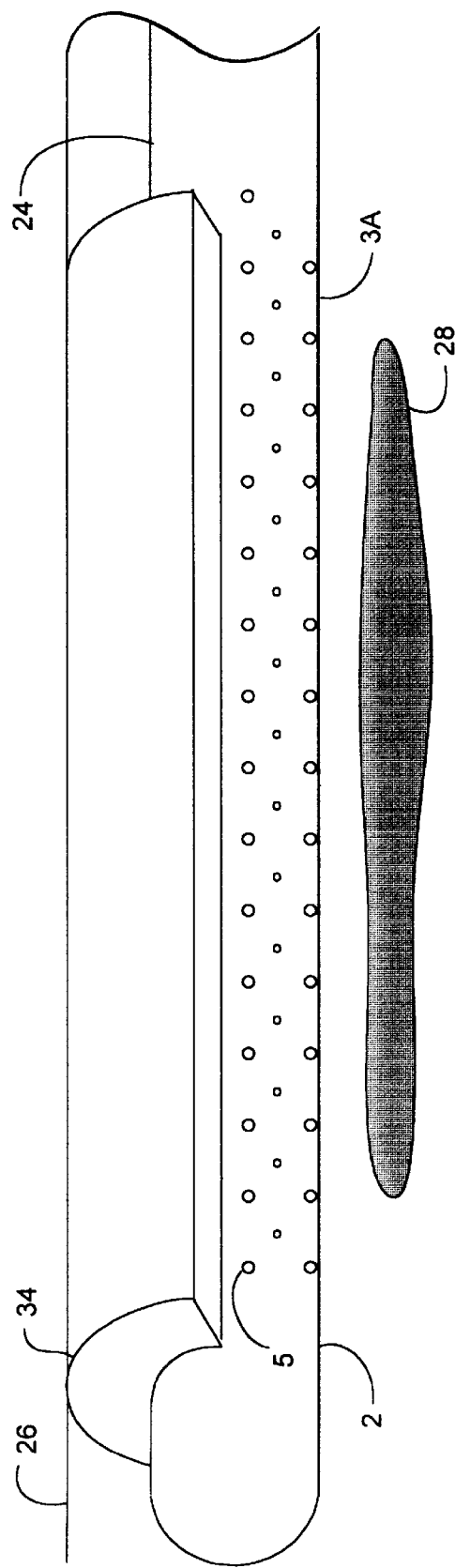
FIG. 11B illustrates the apparatus of FIG. 11A inflated within a body lumen.

As illustrated in FIG. 11 A, the elongated body 24 can include a balloon 34 and an inflation lumen 36. In operation, the balloon 34 can be inflated via the inflation lumen 36. As illustrated in FIG. 11B, inflation of the balloon 34 can serve to drive the tissue contact surface 3A against the side of the body lumen 26. The pressure of the tissue contact surface 3A against the body lumen 26 can serve to create an at least partial seal between the tissue contact surface 3A and the body lumen 26.

Note many of the embodiments described above describe examples of the administration of medicament, but the apparatus 1 of the present invention can also be used for the collection of bodily fluids. For instance, by placing a vacuum suction apparatus 1 against the treated portions of the skin after fine holes 14 are opened in the surface of the living tissue with the apparatus 1, the collection of bodily fluids can be performed efficiently through the skin at low negative pressures. Examples of the collection of bodily fluids include the extraction of sweat, intercellular fluid, blood, blood serum, electrolytes, enzymes, proteins, foreign substances, drugs, poisons or the like.

Note that the various exemplary embodiments described above describe examples of the transdermal administration of medicament, but the present invention is not limited thereto, but rather the present invention can also be applied to the case of administration of medicament or collection of bodily fluids from walls of blood vessels or the surface of organs.

Figure 12:
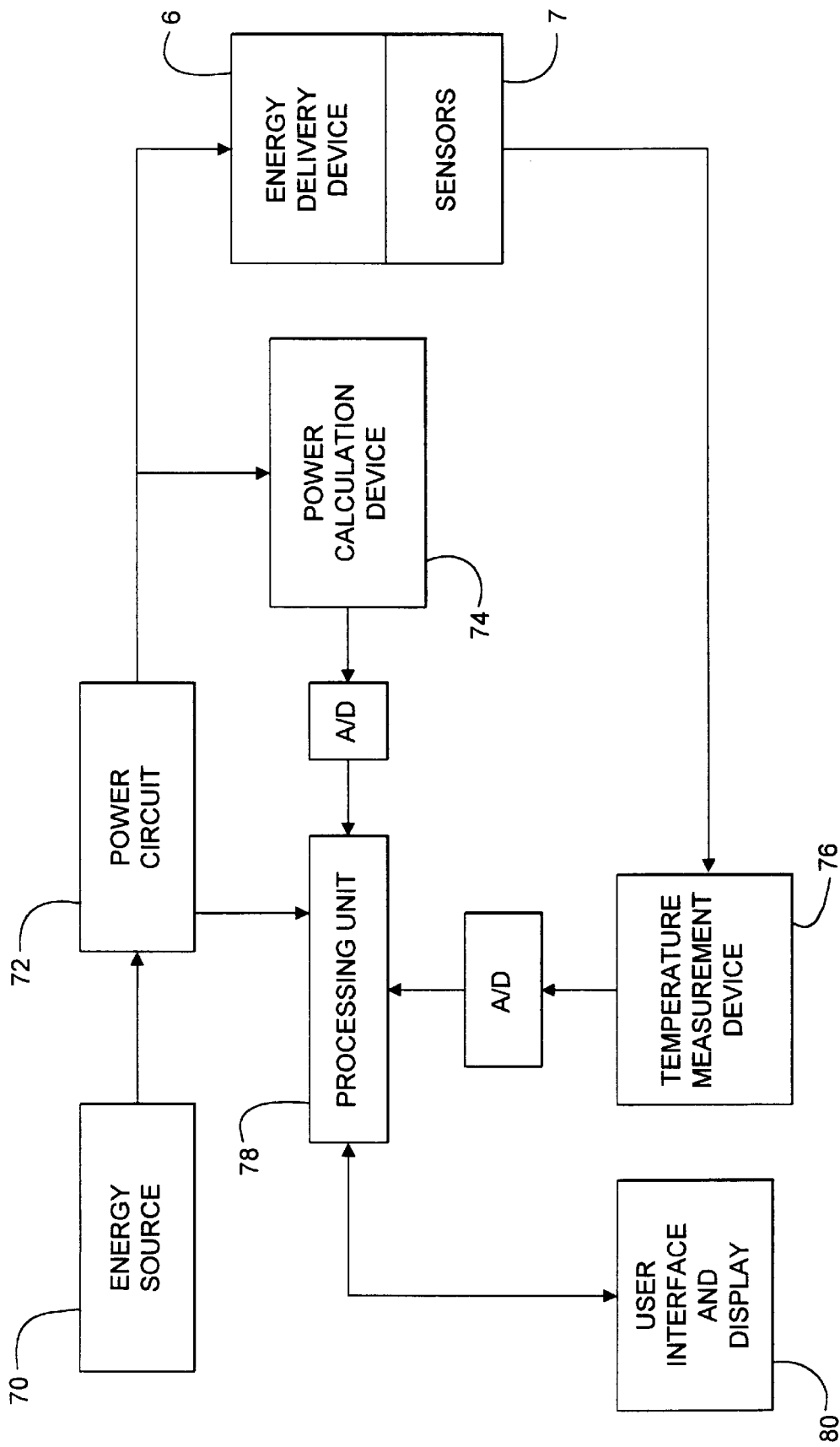
FIG. 12 is a block diagram of feedback control system for use with the apparatus.

The apparatus 1 can be coupled with a feedback control system 68 as illustrated in FIG. 12. The temperature at each temperature sensor 7 is monitored and the output power of energy source adjusted accordingly. The physician can, if desired, override the closed or open loop system.

The feedback control system 68 includes an energy source 70, power circuits 72 and a power calculation device 74 coupled with the energy delivery device 6. A temperature measurement device 76 is coupled with the temperature sensors 7 on the apparatus 1. A processing unit 78 is coupled with the power calculation device 74, the power circuits 72 and a user interface and display 80.

In operation, the temperature at each temperature sensor 7 is determined at the temperature measurement device 76. The processing unit 78 receives each determined temperature from the temperature measurement device 76. The determined temperature can then be displayed to the user at the user interface and display 80.

The processing unit 78 includes logic for generating a temperature control signal. The temperature control signal is proportional to the difference between the measured temperature and a desired temperature. The desired temperature can be determined by the user. The user can set the predetermined temperature at the user interface and display 80.

The temperature control signal is received by the power circuits 72. The power circuits 72 adjust the power level of the energy supplied to the energy delivery device 6 from the energy source 70. For instance, when the temperature control signal is above a particular level, the power supplied to the energy delivery device 6 is reduced in proportion to the magnitude of the temperature control signal. Similarly, when the temperature control signal is below a particular level, the power supplied to the energy delivery device 6 is increased in proportion to the magnitude of the temperature control signal. After each power adjustment, the processing unit 78 monitors the temperature sensors 7 and produces another temperature control signal which is received by the power circuits 72.

The processing unit 78 can also include safety control logic. The safety control logic detects when the temperature at a temperature sensor 7 has exceeded a safety threshold. The processing unit 78 can then provide a temperature control signal which causes the power circuits 72 to stop the delivery of energy from the energy source 70 to the energy delivery device 6.

The power supplied to the ultrasound element may be adjusted in response to the temperature sensor 7 which indicates the highest temperature. Making power adjustments in response to the temperature of the temperature sensor 7 indicating the highest temperature can prevent overheating of the treatment site 28.

The processing unit 78 also receives a power signal from a power calculation device 74. The power signal can be used to determine the power being received by the energy delivery device 6. The determined power can then be displayed to the user on the user interface and display 80.

The feedback control system 68 can maintain the tissue adjacent to the energy delivery device 6 at a desired temperature for a selected period of time.

The processing unit 78 can be a digital or analog controller, or a computer with software. When the processing unit 78 is a computer it can include a CPU coupled through a system bus. The user interface and display 80 can be a mouse, keyboard, a disk drive, or other non-volatile memory systems, a display monitor, and other peripherals, as are known in the art. Also coupled to the bus is a program memory and a data memory.

In lieu of the series of power adjustments described above, a profile of the power delivered to the energy delivery device 6 can be incorporated in the processing unit 78 and a preset amount of energy to be delivered may also be profiled. The power delivered to each energy delivery device 6 can the be adjusted according to the profiles.

The foregoing description of a preferred embodiment of the invention has been presented for purposes of illustration and description. 1t is not intended to be exhaustive or to limit the invention to the precise forms disclosed. Obviously, many modifications, combinations and variations will be apparent to practitioners skilled in this art.

What is claimed is:

1. An apparatus for creating holes in a biological tissue, comprising:
   a housing which at least partially defines a fluid chamber including a tissue contact surface which is configured to be positioned adjacent the biological tissue;
   an ultrasound delivery device positioned adjacent the fluid chamber and configured to cavitate a fluid within the fluid chamber;
   a plurality of apertures extending from the fluid chamber through the tissue contact surface and having a width of about 0.3 $\mu$m to 1 mm;
   an encapsulation sheet adhered to the tissue contact surface to prevent the fluid from leaking from the fluid chamber through the apertures;
   wherein the encapsulation sheet is configured to be punctured by the fluid exiting from the chamber through the apertures in response to operation of the ultrasound delivery device.

2. The apparatus of claim 1, further comprising:
   an adhesive which can bind to the tissue coupled with a distal side of the tissue contact surface.

3. The apparatus of claim 2, further comprising:
   a removable backing coupled with the adhesive.

4. The apparatus of claim 1, further comprising:
   an elongated body coupled with the housing.

5. The apparatus of claim 4, wherein the elongated body includes a fluid delivery lumen in communication with the fluid chamber.

6. The apparatus of claim 5, wherein the elongated body includes an expansion lumen and a balloon configured to be expanded via the expansion lumen.

7. The apparatus of claim 6, wherein the balloon is positioned on an opposite side of the elongated body from the tissue contact surface.

8. The apparatus of claim 4, wherein the elongated body is integral with the housing.

9. The apparatus of claim 1, wherein the ultrasound delivery device is an ultrasound element.

10. The apparatus of claim 9, wherein the ultrasound element is a piezoelectric material.

11. The apparatus of claim 9, wherein the ultrasound element is configured to provide ultrasound energy with a frequency of 10 kHz to 100 MHz.

12. The apparatus of claim 9, wherein the ultrasound is configured to provide an ultrasound energy with an intensity of 0.1–1000 W/cm$^2$.

13. The apparatus of claim 1, further comprising:
at least one temperature sensor.

14. The apparatus of claim 13, further comprising:
a feedback control system for adjusting a level of an energy delivered from the ultrasound delivery device in response to a signal from the at least one temperature sensor.

15. The apparatus of claim 1, further comprising:
a fluid reservoir in fluid communication with the fluid chamber.

16. The apparatus of claim 15, further comprising:
a pump positioned between the fluid chamber and the fluid reservoir.

17. The apparatus of claim 1, further comprising:
a cavitation threshold reducing substance positioned within the apertures.

18. The apparatus of claim 1, wherein the tissue contact surface is constructed from an ultrasound-absorbent material.

19. The apparatus of claim 1, wherein the tissue contact surface is constructed from an ultrasound-reflective material.

20. The apparatus of claim 1, wherein the plurality of apertures have a circular shape.

21. The apparatus of claim 1, wherein the plurality of apertures have a square shape.

22. The apparatus of claim 1, wherein the apertures are uniformly distributed across the tissue contact surface.

23. The apparatus of claim 1, wherein the apertures have a density of 1 to 1 million per square centimeter of tissue contact surface.

24. An apparatus for creating holes in a biological tissue, comprising:
a housing which at least partially defines a fluid chamber including a tissue contact surface which is configured to be positioned adjacent the biological tissue;
an ultrasound delivery device positioned adjacent the fluid chamber and configured to cavitate a fluid within the fluid chamber;
a plurality of apertures extending from the fluid chamber through the tissue contact surface and sized to have the fluid exit from the chamber through the apertures during the cavitation of the fluid; and
an encapsulation sheet adhered to the tissue contact surface to prevent the fluid from leaking from the fluid chamber through the apertures and configured to be punctured by the fluid exiting from the chamber through the apertures in response to operation of the ultrasound delivery device.

25. The apparatus of claim 24, further comprising:
an adhesive which can bind to the tissue coupled with a distal side of the tissue contact surface.

26. The apparatus of claim 25, further comprising:
a removable backing coupled with the adhesive.

27. The apparatus of claim 24, further comprising:
an elongated body coupled with the housing.

28. The apparatus of claim 27, wherein the elongated body includes a fluid delivery lumen in communication with the fluid chamber.

29. The apparatus of claim 28, wherein the elongated body includes an expansion lumen and a balloon configured to be expanded via the expansion lumen.

30. The apparatus of claim 29, wherein the balloon is positioned on an opposite side of the elongated body from the tissue contact surface.

31. The apparatus of claim 27, wherein the elongated body is integral with the housing.

32. The apparatus of claim 24, wherein the ultrasound delivery device is an ultrasound element.

33. The apparatus of claim 32, wherein the ultrasound element is a piezoelectric material.

34. The apparatus of claim 32, wherein the ultrasound element is configured to provide ultrasound energy with a frequency of 10 kHz to 100 MHz.

35. The apparatus of claim 32, wherein the ultrasound is configured to provide an ultrasound energy with an intensity of 0.1–1000 W/cm$^2$.

36. The apparatus of claim 32, wherein the apertures have a width of about 0.1 $\mu$m to 3 mm.

37. The apparatus of claim 32, wherein the apertures have a width of about 0.3 $\mu$m 0.1 mm.

38. The apparatus of claim 24, further comprising:
at least one temperature sensor.

39. The apparatus of claim 38, further comprising:
a feedback control system for adjusting a level of an energy delivered from the ultrasound delivery device in response to a signal from the at least one temperature sensor.

40. The apparatus of claim 24, further comprising:
a fluid reservoir in fluid communication with the fluid chamber.

41. The apparatus of claim 40, further comprising:
a pump positioned between the fluid chamber and the fluid reservoir.

42. The apparatus of claim 24, further comprising:
a cavitation threshold reducing substance positioned within the apertures.

43. The apparatus of claim 24, wherein the tissue contact surface is constructed from an ultrasound-absorbent material.

44. The apparatus of claim 24, wherein the tissue contact surface is constructed from an ultrasound-reflective material.

* * * * *